US009931409B2

(12) United States Patent
Boday et al.

(10) Patent No.: US 9,931,409 B2
(45) Date of Patent: *Apr. 3, 2018

(54) METHODS AND MATERIALS FOR THERAPEUTIC DELIVERY

(71) Applicant: International Business Machines Corporation, Armonk, NY (US)

(72) Inventors: Dylan J. Boday, Austin, TX (US); Jeannette M. Garcia, San Leandro, CA (US); James L. Hedrick, Pleasanton, CA (US); Rudy J. Wojtecki, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/446,658

(22) Filed: Mar. 1, 2017

(65) Prior Publication Data

US 2017/0173170 A1    Jun. 22, 2017

Related U.S. Application Data

(62) Division of application No. 15/080,272, filed on Mar. 24, 2016, which is a division of application No. 14/311,223, filed on Jun. 20, 2014, now Pat. No. 9,352,045.

(51) Int. Cl.
*C08G 12/40* (2006.01)
*A61K 47/48* (2006.01)
*C08G 12/08* (2006.01)

(52) U.S. Cl.
CPC .. *A61K 47/48192* (2013.01); *A61K 47/48215* (2013.01); *C08G 12/08* (2013.01); *C08G 12/40* (2013.01)

(58) Field of Classification Search
CPC ........ A61K 47/34; C08G 12/08; C08G 12/40; C08G 64/0216; C08G 73/06; C08G 73/0644
See application file for complete search history.

(56) References Cited

U.S. PATENT DOCUMENTS

| | | |
|---|---|---|
| 2,889,277 A | 6/1959 | Hughes |
| 3,340,232 A | 9/1967 | Smith et al. |
| 3,598,748 A | 8/1971 | Hirosawa |
| 3,957,742 A | 5/1976 | Kveton |
| 4,106,904 A | 8/1978 | Oude Alink et al. |
| 4,224,417 A | 9/1980 | Hajek et al. |
| 4,225,481 A | 9/1980 | Wagner |
| 4,246,160 A | 1/1981 | Wagner et al. |
| 4,301,262 A | 11/1981 | Wagner et al. |
| 4,839,460 A | 6/1989 | Molzahn |
| 4,877,451 A | 10/1989 | Winnik et al. |
| 5,112,796 A | 5/1992 | Iannicelli |
| 5,674,377 A | 10/1997 | Sullivan, III et al. |
| 5,693,751 A | 12/1997 | Sakurai et al. |
| 5,830,243 A | 11/1998 | Wolak et al. |
| 7,384,434 B2 | 6/2008 | Malfer et al. |
| 8,470,891 B2 | 6/2013 | Hedrick et al. |
| 2009/0039018 A1 | 2/2009 | Jordi et al. |
| 2010/0107476 A1 | 5/2010 | Cosimbescu |
| 2012/0049308 A1 | 3/2012 | Nishimura et al. |
| 2012/0232018 A1 | 9/2012 | Hedrick et al. |
| 2013/0118996 A1 | 5/2013 | Kaplan |
| 2013/0281515 A1 | 10/2013 | Coady et al. |

FOREIGN PATENT DOCUMENTS

| | | |
|---|---|---|
| CN | 101265255 A | 9/2008 |
| EP | 2636697 A1 | 9/2013 |
| GB | 928112 A | 6/1963 |
| GB | 1531578 A | 11/1978 |
| WO | 0166614 A2 | 9/2001 |
| WO | 0198388 A1 | 12/2001 |
| WO | 0226849 A1 | 4/2002 |
| WO | 2012113617 A1 | 8/2012 |

OTHER PUBLICATIONS

"1-Propanol" (http://www.chemspider.com/Chemical-Structure.1004.html) accessed Dec. 15, 2016.*
"Loratadine" (https://livertox.nih.gov/Loratadine_Desloratadine.htm) Mar. 9, 2017.*
Silikas, N. et al. "Rheology of urethane dimethacrylate and diluent formulations" Dental Materials 15 (1999) 257-261.*

(Continued)

*Primary Examiner* — Timothy P Thomas
*Assistant Examiner* — Andrew S Rosenthal
(74) *Attorney, Agent, or Firm* — Patterson + Sheridan, LLP

(57) ABSTRACT

Method for preparing a supramolecular therapeutic agent delivery assembly are provided. A carbonate-containing precursor, a functionalized aliphatic precursor, and an aromatic diamine precursor may be combined to form an amphiphilic block co-polymer. The block co-polymer undergo a cross-linking polymerization process and a therapeutic agent may be incorporated into the resulting supramolecular assembly. The supramolecular assembly may comprise HT, PHT, HA, and/or PHA materials.

15 Claims, 1 Drawing Sheet

(56) References Cited

OTHER PUBLICATIONS

"TCI" (http://www.tcichemicals.com/eshop/en/us/commodity/T1484/index.html?utm_source=SciFinder&utm_medium=referral&utm_campaign=A_commodity_201701) accessed May 22, 2017, pp. 1-2.*

Garcia, J.M. et al. "Recyclable, Strong Thermosets and Organogels via Paraformaldehyde Condensation with Diamines" Science 2014, 344, 732-735.

Henri Ulrich et al., Reaction of Chloromethyl Ether with Primary Amines, May 1961, pp. 1637-1638.

Hemant S. Patel et al., Studies on Synthesis and Characterization of some Novel Aromatic Copolyesters based on s-Triazine, Iranian Polymer Journal, vol. 14, No. 12, 2005, pp. 1090-1098.

Fabian Suriano et al., Functionalized cyclic carbonates: from synthesis and metal-free catalyzed ring-opening polymerization to applications, Polymer Chemistry, The Royal Society of Chemistry, 2011, pp. 528-533.

Wang Yulan et al., Synthesis and Properties of Poly-1, 3, 5-Triazines, Polymer Communications, No. 2, 1984, pp. 117-123.

John Markoff, Error at IBM Lap Finds New Family of Materials, New York Times, May 15, 2014, 4 pages.

Jeanette M. Garcia et al., Recyclable, Strong Thermosets and Organogels via Paraformaldehyde Condensation with Diamines, Science AAAS, vol. 344, May 16, 2014, pp. 732-735.

D.R. Anderson et al., Thermally resistance polymers containing the s-triazine ring, Journal of Polymer Science Part A-1: Polymer Chemistry, vol. 4, Issue 7, pp. 1689-1702, Jul. 1966.

T. Okita, Filter method for the determination of trace quantities of amines, mercaptans, and organic sulphides in the atmosphere, Atmospheric Environment (1967), vol. 4, Issue 1, Jan. 1970, pp. 93-102.

Raquel Lebrero et al., Odor abatement in biotrickling filters: Effect of the EBRT on methyl mercaptan and hydrophobic VOCs removal, Bioresource Technology, Special Issue: Innovative Researches on Algal Biomass, vol. 109, Apr. 2012, pp. 38-45.

Elbert et al "Conjugate Addition Reactions Combined with Free-Radical Cross-Linking for the Design of Materials for Tissue Engineering," Biomacromolecules 2001, 2, 430-441; Published on Web Mar. 3, 2001.

Ferrar, "Reactions of Formaldehyde With Aromatic Amines," J. Appl. Chem, 14, 1964, 389-399.

Geng, et al., "Nanoindentation behavior of ultrathin polymeric films," Polymer 46 (2005) 11768-11772; Available online Oct. 19, 2005.

Hiller, et al., "Laser-engravable hexahydrotriazine polymer networks," Mat Res Innovat (2002) 6:179-184.

Oliver, et al. "Measurement of hardness and elastic modulus by; instrumented indentation: Advances in understanding and; refinements to methodology," J. Mater. Res., vol. 19, No. 1, Jan. 2004, 3-20.

Singh, et al., "Ultrasound mediated Green Synthesis of Hexa-hydro Triazines," J. Mater. Environ. Sci. 2 (4) (2011) 403-406.

Stafford, et al., "A buckling-based metrology for measuring; the elastic moduli of polymeric thin films," Nature Materials. sub.—3.sub.—Aug. 2004, 545-550;Published online: Jul. 11, 2004.

Ekinci et al., "Preparation, Characterization and H2O2 Selectivity of Hyperbranched Polyimides Containing Triazine", Journal of Polymer Research, 2005, pp. 205-210.

International Search Report and Written Opinion for International Application No. PCT/US15/36428 dated Jun. 18, 2015.

"Precursor" (https://www.merriam-webster.com/dictionary/precursor) accessed Dec. 15, 2016.

"1-Propanol" (http://www.chemspider.com/Chemicai-Structure.1004.html) accessed Dec. 15, 2016.

"Sodium Carbonate" (http://www.chemspider.com/Chemicai-Structure.9916.html) accessed Dec. 15, 2016.

Kabanov, A.V. et al. "Piuronic block copolymers: novel functional molecules for gene therapy" Advanced Drug Delivery Reviews; 54(2002)223-233.

"List of IBM Patents or Applications Treated as Related".

Tomas Torres and Giovanni Bottari, "Organic Nanomaterials Cynthesis, Characterization, and Device Applications," 3 pages, Oct. 2013.

Ruchit Trivedi and Uday B Kompella, "Nanomicellar formulations for sustained drug delivery: strategies and underlying principles," Published in final edited form as: Nanomedicine (Lond). Apr. 2010 ; 5(3): 485-505. doi:10.2217/nnm.10.10.

* cited by examiner

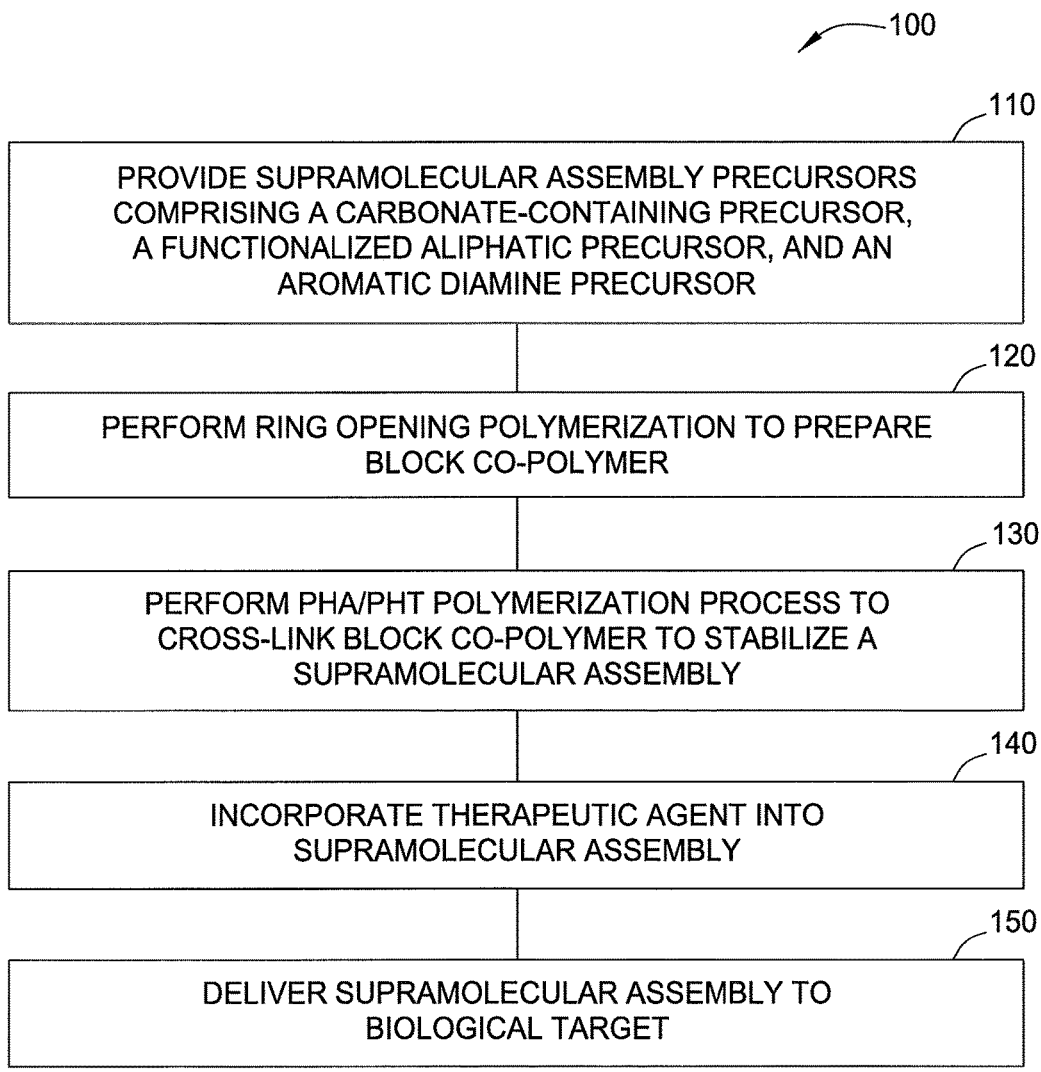

METHODS AND MATERIALS FOR THERAPEUTIC DELIVERY

CROSS-REFERENCE TO RELATED APPLICATIONS

This application is a divisional of and claims benefit to co-pending U.S. Divisional patent application Ser. No. 15/080,272, filed Mar. 24, 2016 and U.S. patent application Ser. No. 14/311,223, filed Jun. 20, 2014, the entirety of which are herein incorporated by reference.

BACKGROUND

The present disclosure relates to a supramolecular assembly for therapeutic agent delivery, and more specifically, to the use of hexahydrotriazine (HT) and hemiaminal (HA) molecules, oligomers, and polymers derived from aromatic, aliphatic, and/or polyether diamines to create carbonate containing supramolecular therapeutic agent delivery assemblies.

Biodegradable polymers are receiving increasing attention in a wide variety of medical and pharmaceutical applications. Synthetic polymers are of particular interest as the synthetic polymers may provide desirable versatility in delivering various therapeutic agents. Synthetic polymers may be tailored, copolymerized or produced with variations in operational conditions to tune specific properties or target specific needs or applications. Various properties of synthetic polymers that may be selectively modified include hydrophobicity, crystallinity, degradability, solubility, and resistivity to specific pH conditions, among others. These synthetic polymers may be configured to provide therapeutic agents in topical or oral delivery applications. Typical components of oral delivery applications include polymers, such as polystyrene or polyacrylates, utilized as a non-degradable scaffold which is physically blended with the therapeutic agent. The polymers are then passed through the intestine intact after digestion. However, currently utilized polymers often lack characteristics which allow for highly targeted therapeutic delivery. Consequently, the therapeutic agent is delivered with a reduced degree localized metabolism specificity with little or no control over the rate at which the therapeutic agent enters the bloodstream.

Thus, what is needed in the art are improved materials for therapeutic agent delivery.

SUMMARY

In one embodiment, a method of preparing a supramolecular therapeutic agent delivery assembly is provided. The method includes providing a first precursor, a second precursor, and a third precursor. A ring opening polymerization may be performed to form a block co-polymer. The block co-polymer may be cross linked by performing a polymerization process to form a supramolecular assembly and a therapeutic agent may be incorporated into the supramolecular assembly.

In another embodiment, a method of preparing a supramolecular therapeutic agent delivery assembly is provided. The method includes providing a carbonate-containing precursor, a functionalized aliphatic precursor, and an aromatic diamine precursor. A ring opening polymerization may be performed to form a block co-polymer. A PHT material may be formed to cross-link the block co-polymer to form a supramolecular assembly and a therapeutic agent may be incorporated into the supramolecular assembly.

In yet another embodiment, a method of preparing a supramolecular therapeutic agent delivery assembly is provided. The method includes providing a first precursor, a second precursor, and a third precursor. A ring opening polymerization may be performed to form a block co-polymer. The block co-polymer may be cross-linked by performing a polymerization process to form a supramolecular assembly. The supramolecular assembly may comprise an HT material having a plurality of trivalent hexahydrotriazine groups having the structure

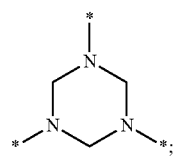

and
a plurality of divalent bridging groups having the structure

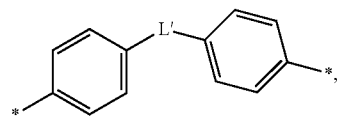

each divalent bridging group bonded to two of the trivalent hexahydrotriazine groups, wherein L' is a divalent linking group. A therapeutic agent may also be incorporated into the supramolecular assembly.

BRIEF DESCRIPTION OF THE SEVERAL VIEWS OF THE DRAWINGS

FIG. 1 illustrates a flow diagram summarizing a method of forming a supramolecular therapeutic agent delivery assembly according to one embodiment.

DETAILED DESCRIPTION

Hexahydrotriazine (HT) materials and hemiaminal (HA) materials derived from aromatic, aliphatic, and/or polyether diamines may be used as a platform for creating supramolecular therapeutic agent delivery assemblies. The supramolecular therapeutic agent delivery assembly may be prepared from a carbonate precursor, a functionalized aliphatic precursor, and an aromatic diamine precursor. The precursors may be utilized to prepare a block co-polymer. The supramolecular therapeutic agent delivery assembly may include single molecule species, oligomers, and/or polymers (i.e., polyhexahydrotriazine, PHT, polyhemiaminal, PHA). The supramolecular therapeutic agent delivery assembly may be made using an aromatic diamine to react with a formaldehyde (i.e. formaldehyde or paraformaldehyde) to facilitate polymeric cross-linking of the block co-polymer. Such supramolecular therapeutic agent delivery assemblies will generally form a micellular structure within which a therapeutic agent may be incorporated. In certain embodiments, the supramolecular assembly may be defined in an aqueous environment. A carbonate moiety of the supramolecular therapeutic agent delivery assembly may be configured to selectively deliver the therapeutic agent within a desired biological environment.

FIG. 1 is a flow diagram summarizing a method 100 of forming a supramolecular therapeutic agent delivery assembly according to one embodiment. At operation 110 various precursors for forming the supramolecular therapeutic agent delivery assembly are provided. In one embodiment, the precursors may include a carbonate-containing precursors (B, C), and an aromatic diamine precursor (A). Exemplary precursors are shown below.

In another embodiment, the precursors may include an aromatic diamine precursor (A), a carbonate/PEG precursor (B), and a cyclic carbonate precursor (C). Exemplary precursors are shown below.

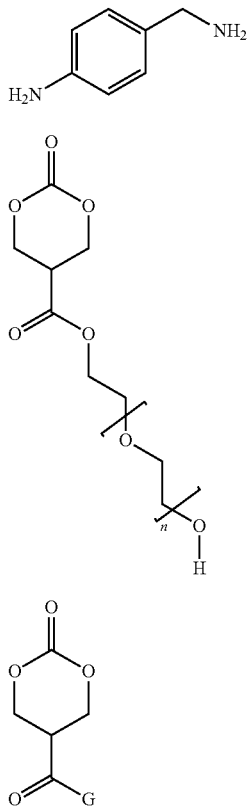

G = carbohydrate, guanidinium, carboxylic acids, alkyl, aryl, amines, alcohols, thiols, dyes, therapeutics, targeting agents.

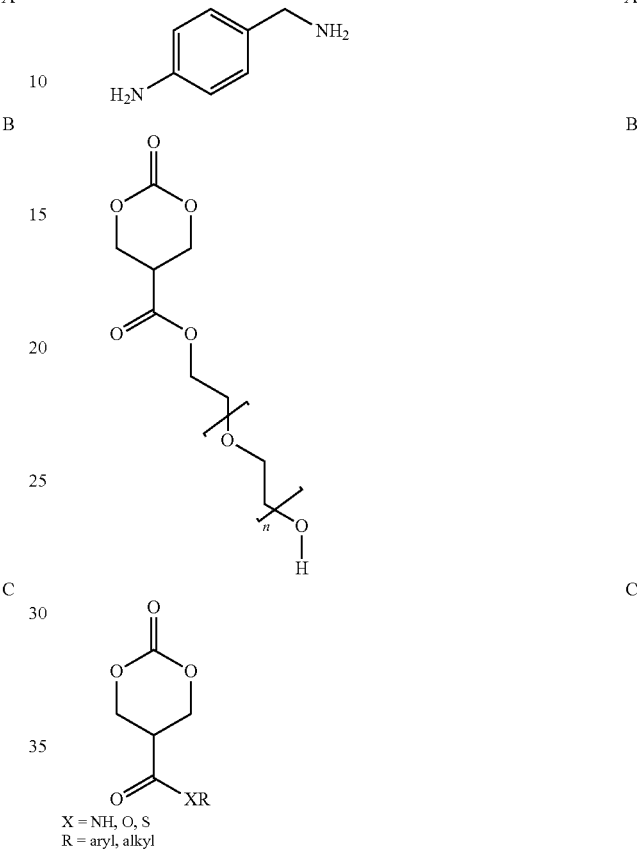

X = NH, O, S
R = aryl, alkyl

A hydrophobic carbonate-containing precursor is shown above and represented as C. The carbonate-containing precursor may be a cyclic carbonate prepared from various materials under suitable process conditions. In one embodiment, the cyclic carbonate precursor may be prepared from 6-hydroxymethyl propionic acid. Although depicted as comprising a 6 member ring, the cyclic carbonate may include a 5-member ring or a 7-member ring. The carbonate-containing precursor may also include a carbonyl moiety. The carbonyl moiety may be bound to a functional group (G), which may be a functional group or a radical. The functional group may be selected from one or more of an amine containing molecule, an oxygen containing molecule, or a sulfur containing molecule, and combinations thereof. The functional group (G) may be bound to the inorganic molecule and may be an aryl substituent, an alkyl substituent, or a combination thereof. In one embodiment, the functional group (G) may include one or more pentafluorophenyl esters. It is contemplated that any suitable cyclic carbonate that exhibits desirable hydrophobic characteristics and pH selectivity may be utilized.

The aromatic diamine precursor is shown above and represented as A. The aromatic diamine precursor may be an amino aniline monomer prepared from various materials under suitable process conditions. In one embodiment, the aromatic diamine precursor may be 4-(aminomethyl)aniline, however it is contemplated that various other aromatic diamines may be utilized.

At operation 120, a ring opening polymerization may be utilized to prepare a block co-polymer. In one embodiment, the ring opening polymerization is an organocatalytic ring opening polymerization. The carbonate-containing precursor (C), the carbonate/PEG precursor (B), and the aromatic diamine precursor (A) may be reacted under conditions suitable to form the block co-polymer composed of varying stoichiometry of the precursors.

The carbonate-containing precursor, the carbonate/PEG precursor, and the aromatic diamine may be combined in a solution comprising a solvent, which may be dichloromethane (DCM), and an organic catalyst, such as diazabicyloundecene (DBU). The reaction may proceed at room temperature for about 3 hours and the resulting block co-polymer may be precipitated in methanol. The reaction conditions may facilitate formation of the block co-polymer at the non-aniline amine due to the reduced nucleophilicity of the aromatic diamine precursor. Thus, the cyclic carbonate may react with the aliphatic amine. As such, the resulting block co-polymer may be end terminated with the aromatic diamines.

In another embodiment, the aromatic diamine precursor (A) may be reacted under suitable conditions with the carbonate/PEG precursor (B) to form the block co-polymer. In one embodiment, the reaction may be a ring opening polymerization, such as an organocatalytic ring opening polymerization. An exemplary block co-polymer according to this embodiment is shown below.

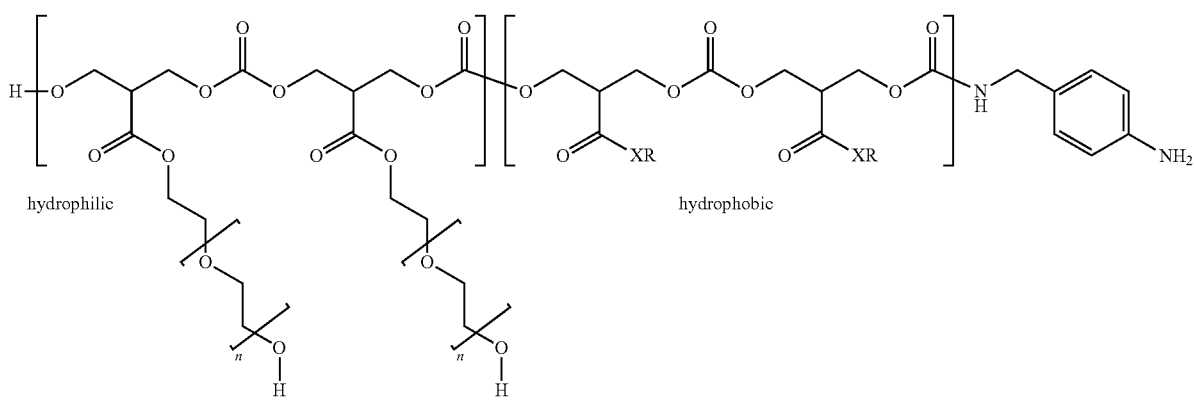

In this embodiment, the resulting block co-polymer has a hydrophobic component (cyclic carbonate precursor (C)) and a hydrophilic component (carbonate/PEG precursor (B)). The aromatic diamine precursor (A) may be disposed on a terminus of the hydrophobic component of the block co-polymer. In this embodiment, the block co-polymer may be considered monofunctional. However, it is contemplated that the addition of various functional groups, for example, amines or proteins, may be integrated with the aromatic diamine precursor (A) to improve therapeutic agent delivery selectivity and cross-linking during a subsequent polymerization process.

In another embodiment, the aromatic diamine precursor (A) may be reacted under suitable conditions with the cyclic carbonate precursor (C) to form the block co-polymer. In one embodiment, the reaction may be a ring opening polymerization, such as an organocatalytic ring opening polymerization. An exemplary block co-polymer according to this embodiment is shown below.

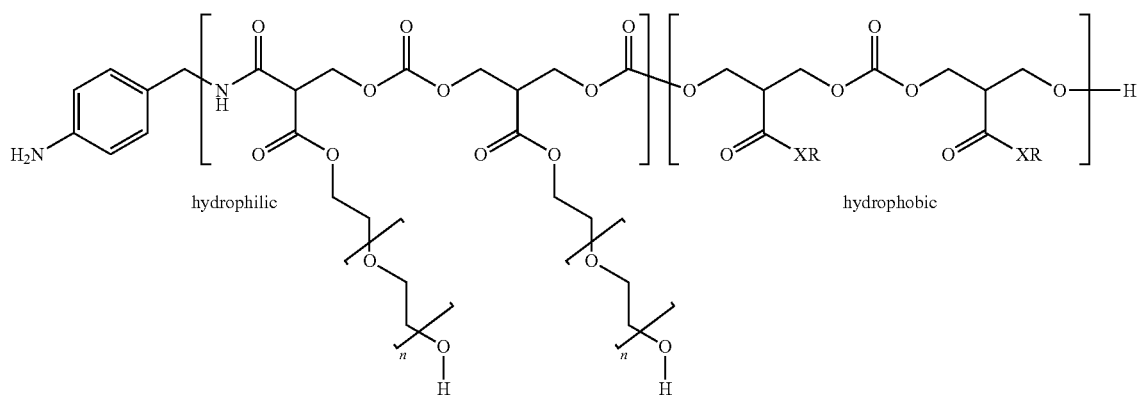

In this embodiment, the resulting block co-polymer has a hydrophobic component (cyclic carbonate precursor (C)) and a hydrophilic component (carbonate/PEG precursor (B)). The aromatic diamine precursor (A) may be disposed on a terminus of the hydrophilic component of the block co-polymer. In this embodiment, the block co-polymer may be considered monofunctional. However, it is contemplated that the addition of various functional groups, for example, amines or proteins, may be integrated with the aromatic diamine precursor (A) to improve therapeutic agent delivery selectivity and cross-linking during a subsequent polymerization process.

The block co-polymer may be an amphiphilic co-polymer. In one embodiment, the hydrophilic component (functionalized aliphatic precursor (A) or carbonate/PEG precursor (B)) of the block co-polymer and the hydrophobic component (carbonate-containing precursor(C)) of the block co-polymer may be present in varying amounts. For example, the ratio of the hydrophilic component to the hydrophobic component may be between about 80:20 and about 60:40, such as about 70:30. Due to the amphiphilic nature of the block co-polymer, the block co-polymer may self-assemble into a micelle in an aqueous environment. For example, the hydrophobic carbonate component of the block co-polymer may be surrounded by the hydrophilic functionalized aliphatic component. Polymer molecules may form a micelle structure by arranging themselves in a spherical pattern with the hydrophobic component of each molecule pointing toward the center of the sphere and the hydrophilic component of each molecule pointing toward the surface of the sphere.

At operation 130, a HT, polyhexahydrotriazine (PHT), HA, or polyhemiaminal (PHA) polymerization process may be performed to cross-link the block co-polymer. The supramolecular assembly is formed spontaneously upon the addition of water and this dynamic assembly can be stabilized by crosslinking of the periphery or the core. In one example, the aromatic diamine component of the block co-polymer, such as 4-(aminomethyl)aniline, may be reacted with a formaldehyde (i.e. paraformaldehyde and subsequently cured to enhance covalent cross-linking of the block co-polymer via condensation reactions. In one embodiment, the curing may be performed by heating the block co-polymer to between about 50° C. and about 280° C., such as greater than about 180° C., for example, about 200° C. Examples according to various embodiments described above are shown below.

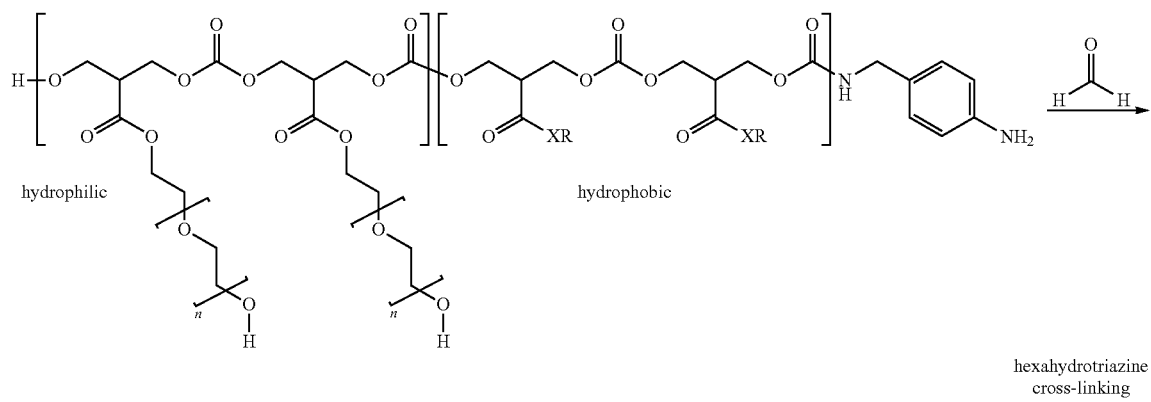

hydrophilic hydrophobic hexahydrotriazine cross-linking

In the embodiment shown above, the polymerization process of operation 130 may result in increased cross-linking of the hydrophobic component which is the core of the micellular supramolecular assembly as compared to the hydrophilic shell component of the micellular supramolecular assembly. The localized cross-linking results from the relationship between the hydrophobic component and the aromatic diamine during the polymerization process of operation 130. Thus, tuning of the core of the micellular structure may be improved to mitigate dynamic assembly of the supramolecular assembly.

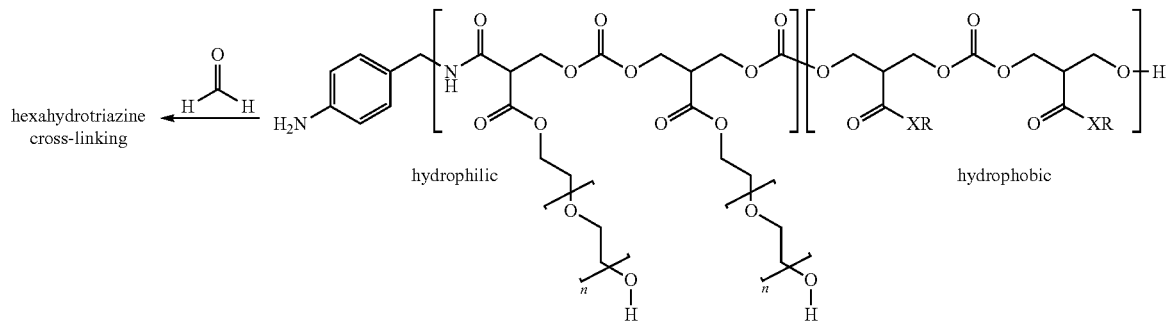

hexahydrotriazine cross-linking hydrophilic hydrophobic

In the embodiment shown above, the polymerization process of operation 130 may result in increased cross-linking of the hydrophilic component which is the shell of the micellular supramolecular assembly as compared to the hydrophobic core component of the micellular supramolecular assembly. The localized cross-linking results from the relationship between the hydrophilic component and the aromatic diamine during the polymerization process of operation 130. Thus, tuning of the periphery of the micellular structure may be improved to mitigate dynamic assembly of the supramolecular assembly.

A PHT material suitable for forming an the supramolecular therapeutic agent delivery assembly as described herein is a molecule, oligomer, or polymer that has a plurality of trivalent hexahydrotriazine groups having the structure and
a plurality of divalent bridging groups of formula (2):

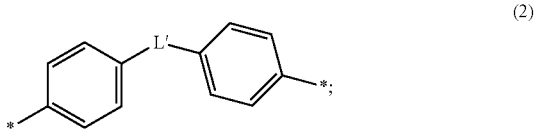

wherein L' is a divalent linking group selected from the group consisting of *—O—*, *—S—*, *—N(R')—*, *—N(H)—*, *—R"—*, and combinations thereof, wherein R' comprises at least 1 carbon and R" comprises at least one carbon, each starred bond of a given hexahydrotriazine group is covalently linked to a respective one of the divalent bridging groups, and each starred bond of a given bridging group is linked to a respective one of the hexahydrotriazine groups. In one embodiment, R' and R" are independently selected from the group consisting of methyl, ethyl, propyl, isopropyl, phenyl, and combinations thereof. Other L' groups include methylene (*-CH$_2$—*), isopropylidenyl (*—C(Me)$_2$-*), and fluorenylidenyl:

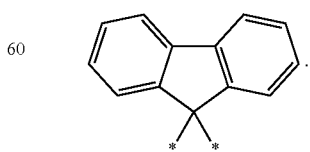

For PHT materials with bridging groups of formula (2), the HT may be represented by formula (3):

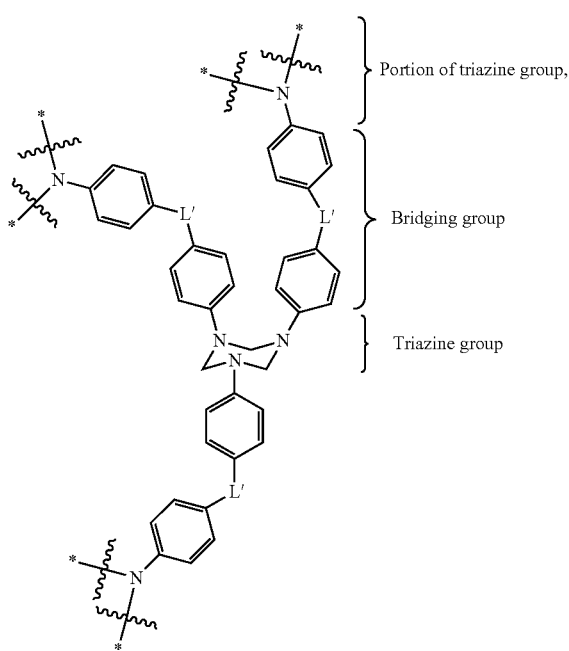

(3)

Portion of triazine group,

Bridging group

Triazine group wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (3) is a portion of a different hexahydrotriazine group.

The PHT may also be represented by the notation of formula (4):

covalently linked to a respective one of the hexahydrotriazine groups. Polymer molecules may be capped or terminated by a capping group in place of a bridging group in formulas (3) and (4). Examples of capping groups include $CH_3$, hydrogen atoms, ether groups, thioether groups, and dimethyl amino groups.

The PHT or HT can be bound non-covalently to water and/or a solvent (e.g., by hydrogen bonds).

Exemplary non-limiting divalent bridging groups include:

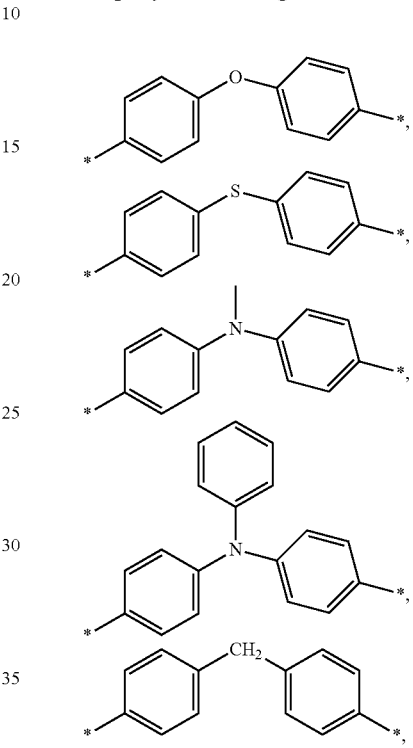

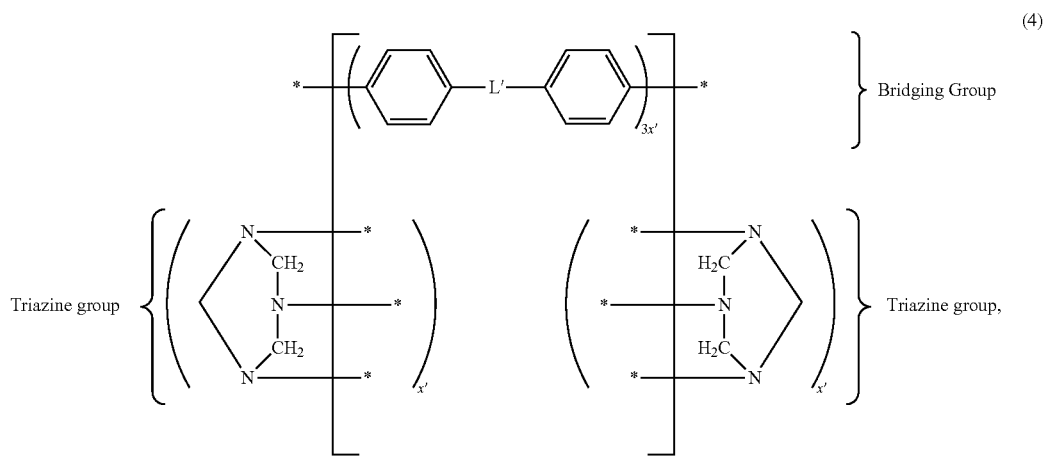

wherein x' is moles, L' is a divalent linking group selected from the group consisting of *—O—*, *—S—*, *—N(R')—*, *—N(H)—*, *—R"—*, and combinations thereof, wherein R' comprises at least 1 carbon and R" comprises at least one carbon. Each starred bond of a given hexahydrotriazine group of formula (4) is covalently linked to a respective one of the bridging groups. Additionally, each starred bond of a given bridging group of formula (2) is -continued

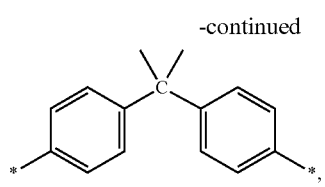

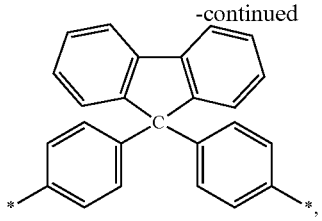

and combinations thereof.

A suitable PHT material may be made by forming a first mixture comprising i) one or more monomers comprising two aromatic primary amine groups, ii) an optional diluent monomer comprising one aromatic primary amine group, iii) paraformaldehyde, formaldehyde, and/or another suitable aldehyde, and iv) a solvent, and heating the first mixture at a temperature of about 50° C. to about 300° C., preferably about 165° C. to about 200° C., thereby forming a second mixture comprising a polyhexahydrotriazine. The heating time at any of the above temperatures can be for about 1 minute to about 24 hours. Diamine monomers suitable for making such PHT materials may have the general structure $H_2N$—Ar-L'-Ar—N—$H_2$, where Ar denotes a benzene ring group and L' is defined as described above. Diluent monomers suitable for including in the reaction are typically primary monoamines $RNH_2$, where the group R bonded to nitrogen has a structure according to formula (5), formula (6), formula (7), and/or formula (8):

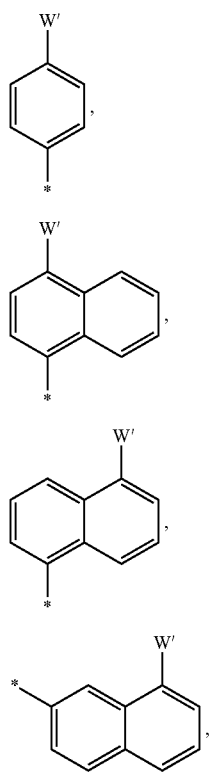

wherein W' is a monovalent radical selected from the group consisting of *—$N(R^1)(R^2)$, *—$OR^3$, —$SR^4$, wherein $R^1$, $R^2$, $R^3$, and $R^4$ are independent monovalent radicals comprising at least 1 carbon. The starred bonds in formulas (5), (6), (7), and (8) denote bonds with the nitrogen atom of the primary amine monomer. Non-limiting exemplary diluent groups include:

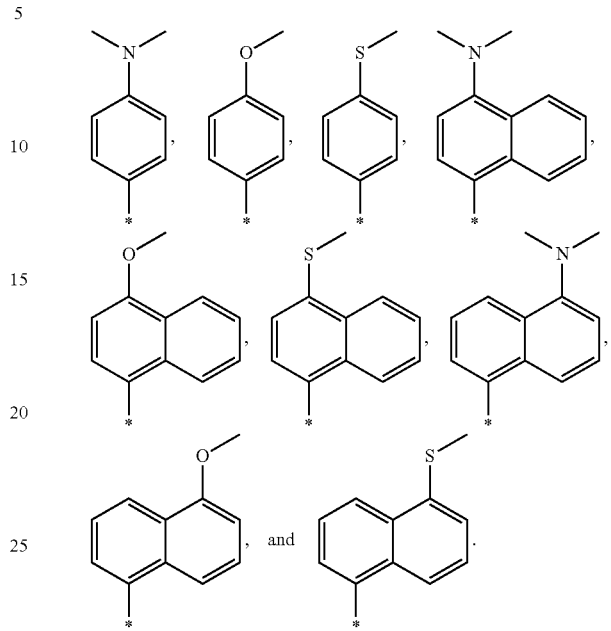

Diluent groups can be used singularly or in combination.

Non-limiting exemplary monomers comprising two primary aromatic amine groups include 4,4'-oxydianiline (ODA), 4,4'-methylenedianiline (MDA), 4,4'-(9-fluorenylidene)dianiline (FDA), p-phenylenediamine (PD), 1,5-diaminonaphthalene (15DAN), 1,4-diaminonaphthalene (14DAN), and benzidene, which have the following structures:

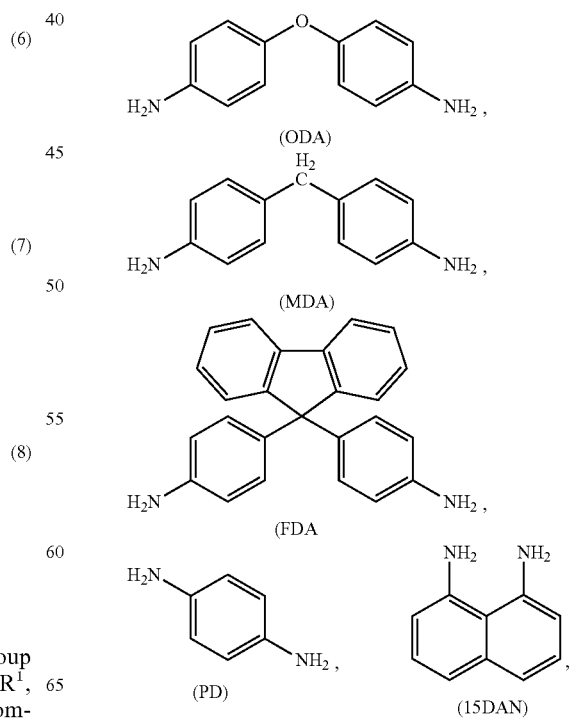

-continued

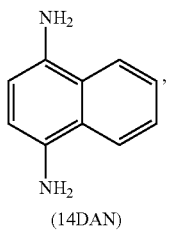
(14DAN)

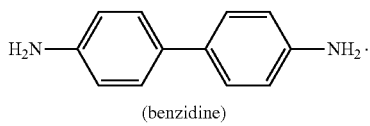
(benzidine)

Non-limiting exemplary diluent monomers include N,N-dimethyl-p-phenylenediamine (DPD), p-methoxyaniline (MOA), p-(methylthio)aniline (MTA), N,N-dimethyl-1,5-diaminonaphthalene (15DMN), N,N-dimethyl-1,4-diaminonaphthalene (14DMN), and N,N-dimethylbenzidene (DMB), which have the following structures:

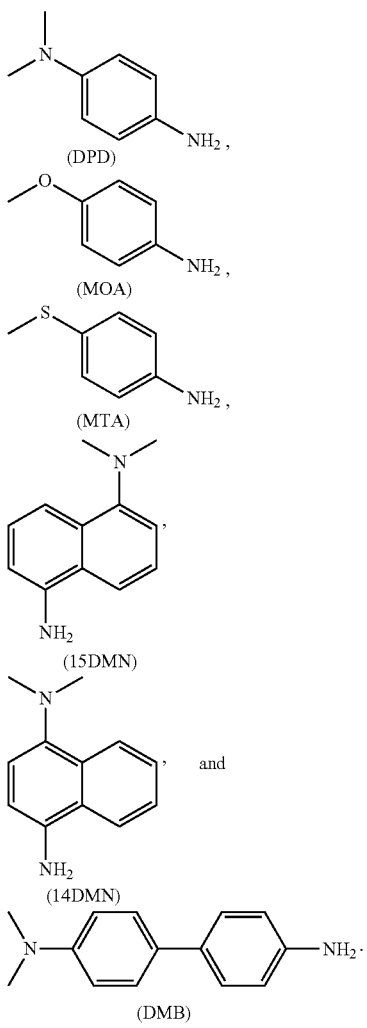

HT and HA materials may be used to cross-link the block co-polymer and provide a scaffold structure for incorporation of a therapeutic agent. It should be noted that many diamines will react with aldehydes, such as formaldehyde, to cross-link the block co-polymer. Alkyl diamines, such as hexane diamine, will also react with formaldehyde to cross-link the block co-polymer. The polyether and alkyl derived materials may form gels, oligomers, and small molecules that are usable as a therapeutic agent delivery assembly.

A related material that may be used to cross-link the block co-polymer is a hemiaminal (HA) material. A polyhemiaminal (PHA) is a crosslinked polymer comprising i) a plurality of trivalent hemiaminal groups of formula (9):

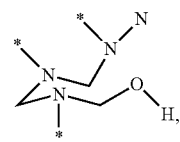

(9)

covalently linked to ii) a plurality of bridging groups of formula (10):

$$K'\!\!-\!\!(*)_{y'} \quad (10),$$

wherein y' is 2 or 3, and K' is a divalent or trivalent radical comprising at least one 6-carbon aromatic ring. In formulas (9) and (10), starred bonds represent attachment points to other portions of the chemical structure. Each starred bond of a given hemiaminal group is covalently linked to a respective one of the bridging groups. Additionally, each starred bond of a given bridging group is covalently linked to a respective one of the hemiaminal groups.

As an example, a polyhemiaminal can be represented by formula (11):

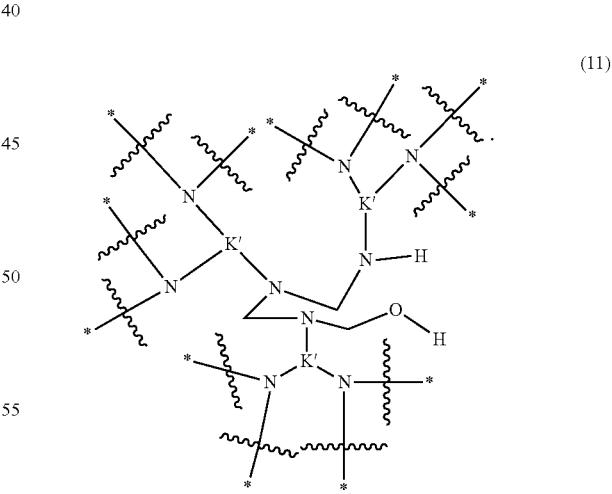

(11)

In this instance, each K' is a trivalent radical (y'=3) comprising at least one 6-carbon aromatic ring. It should be understood that each nitrogen having two starred wavy bonds in formula (11) is a portion of a different hemiaminal group.

The structure of formula (11) can also be represented using the notation of formula (12):

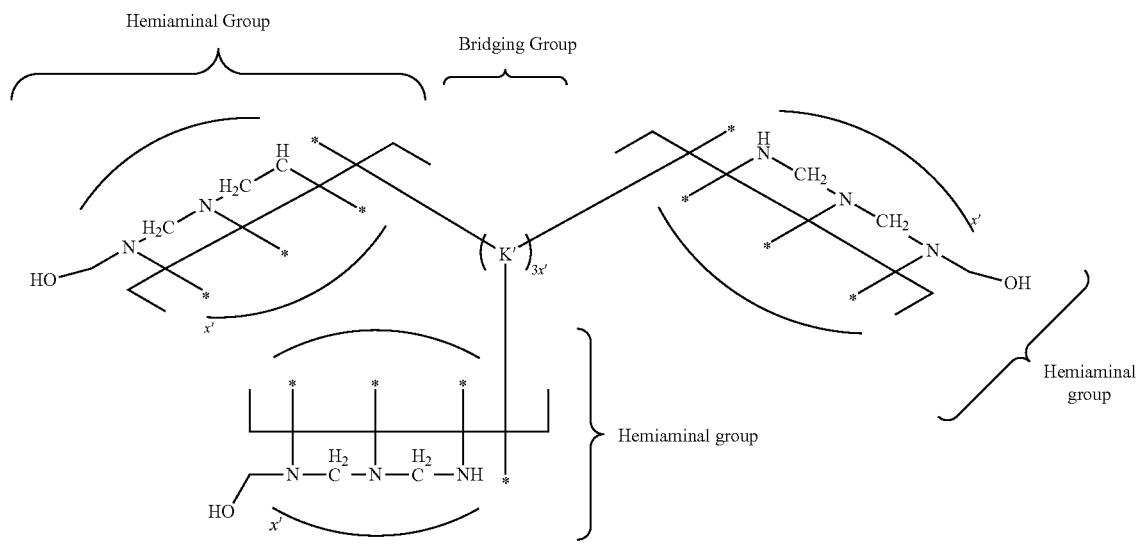

(12), wherein x' is moles and each bridging group K' is a trivalent radical (y'=3 in formula (10)) comprising at least one 6-carbon aromatic ring. It should be understood that each starred nitrogen bond of a given hemiaminal group of formula (12) is covalently linked to a respective one of the bridging groups K'. Additionally, each starred bond of a given bridging group K' of formula (12) is covalently linked to a respective one of the hemiaminal groups.

Non-limiting exemplary trivalent bridging groups for HA materials include:

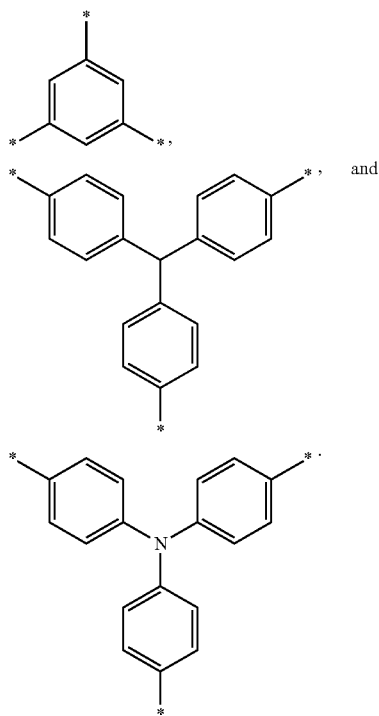

The bridging groups can be used singularly or in combination.

Polyhemiaminals composed of divalent bridging groups K' can be represented herein by formula (13):

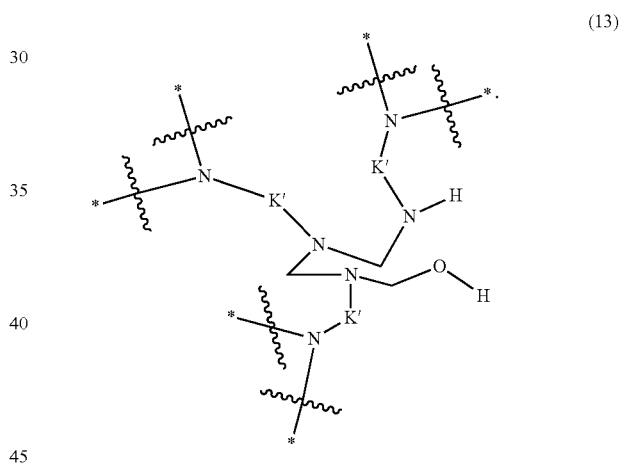

wherein K' is a divalent radical (y'=2 in formula (10)) comprising at least one 6-carbon aromatic ring. Each nitrogen having two starred wavy bonds in formula (13) is a portion of a different hemiaminal group.

More specific divalent bridging groups have the formula (14):

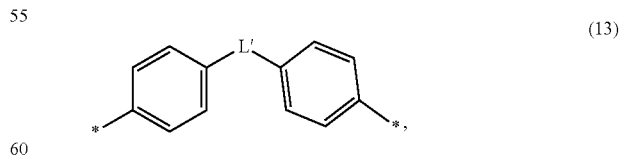

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. In an embodiment, R' and R" are independently selected from the group consisting of methyl, ethyl, propyl, isopropyl, phenyl, and combinations thereof. Other L' groups include methylene (*—$CH_2$—*), isopropylidenyl (*—$C(Me)_2$-*), and fluorenylidenyl:

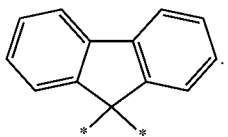 [SMILES: *C1(*)c2ccccc2-c2ccccc21]

Polyhemiaminals composed of divalent bridging groups of formula (14) can be represented herein by formula (15):

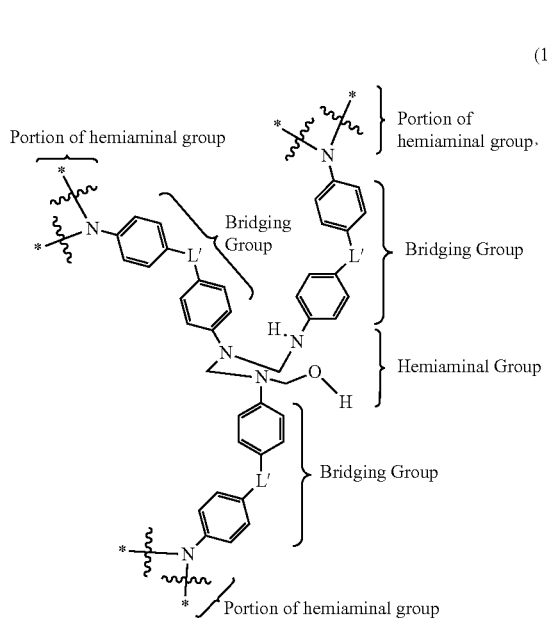

(15)

wherein L' is a divalent linking group selected from the group consisting of *—O—*, *—S—*, *—N(R')—*, *—N(H)—*, *—R"—*, and combinations thereof, wherein R' and R" independently comprise at least 1 carbon. Each nitrogen having two starred wavy bonds in formula (15) is a portion of a different hemiaminal group.

The polyhemiaminal of formula (15) can also be represented by the notation of formula (16):

wherein x' is moles, and L' is a divalent linking group selected from the group consisting of *—O—*, *—S—*, *—N(R')—*, *—N(H)—*, *—R"—*, and combinations thereof, wherein R' and R" independently comprise at least 1 carbon. Each starred nitrogen bond of a given hemiaminal group of formula (16) is covalently linked to a respective one of the bridging groups. Additionally, each starred bond of a given bridging group of formula (16) is covalently linked to a respective one of the hemiaminal groups.

The hemiaminal groups can be bound non-covalently to water and/or a solvent. A non-limiting example is a hemiaminal group that is hydrogen bonded to two water molecules as shown in formula (17):

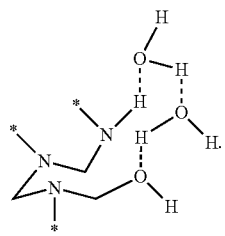

(17)

In some embodiments, a hemiaminal material may form a covalent network with water molecules that may be a polyhemiaminal hydrate (PHH). A PHA material of this form may be made, for example, by reaction of polyethylene glycol oligomers with paraformaldehyde. Such materials may be organogels in some cases.

Typical HT and HA polymers and oligomers, and PHH materials, as described herein may be disassembled in aqueous solutions. HT oligomers and polymers will disassemble into monomers and may dissolve in acid solutions having pH less than about 3, such as less than about 2.5, for example less than about 2.

An HA material suitable for use according to the methods described herein may be made using the same groups of reactants as for the HT materials. The diluent monomers described above may also be used to make HA materials. A method of preparing a polyhemiaminal (PHA) comprising divalent bridging groups comprises forming a first mixture comprising i) a monomer comprising two or more primary aromatic amine groups, ii) an optional diluent monomer comprising one aromatic primary amine group, iii) paraformaldehyde, and iv) a solvent. The first mixture is then preferably heated at a temperature of about 20° C. to about 120° C. for about 1 minute to about 24 hours, thereby forming a second mixture comprising the PHA. In an embodiment, the monomer comprises two primary aromatic

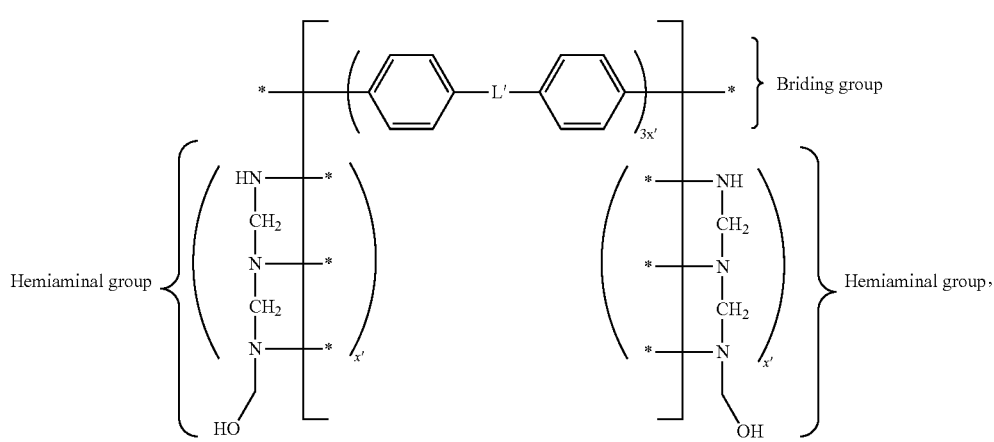

(16)

amine groups. The mole ratio of paraformaldehyde: total moles of primary aromatic amine groups (e.g., diamine monomer plus optional monoamine monomer) may be about 1:1 to about 1.25:1, based on one mole or equivalent of paraformaldehyde equal to 30 grams. The solvent can be any suitable solvent. Exemplary solvents include dipolar aprotic solvents such as, for example, N-methyl-2-pyrrolidone (NMP), dimethylsulfoxide (DMSO), N,N-dimethylformamide (DMF), N,N-dimethylacetamide (DMA), Propylene carbonate (PC), N-cyclohexyl-2-pyrrolidone (CHP), N,N'-dimethylpropyleneurea (DMPU), and propylene glycol methyl ether acetate (PGMEA).

A PHT material may be prepared from a PHA material. The PHT can be prepared by heating a solution comprising the PHA at a temperature of at least 50° C., such as about 165° C. to about 280° C. or about 180° C. to about 220° C., for example at about 200° C. for about 1 minute to about 24 hours. Additionally, a mixed PHA/PHT copolymer may be made by partially converting a PHA material to a PHT material. A combination of low conversion temperature, for example about 150° C. to about 165° C., and short conversion time, for example about 1 minute to about 10 minutes, may be used to make a mixed PHA/PHT material.

An exemplary PHA material may be made by reaction of 4,4'-oxydianiline (ODA) with paraformaldehyde (PF). The product is a powder or solid plastic.

4,4'-Oxydianiline (ODA, 0.20 g, 1.0 mmol) and paraformaldehyde (PF, 0.15 g, 5.0 mmol, 5 equivalents (eq.)) were weighed out into a 2-Dram vial inside a $N_2$-filled glovebox. N-methylpyrrolidone (NMP, 6.2 g, 6.0 mL, 0.17 M) was added. The vial was capped but not sealed. The reaction mixture was removed from the glovebox, and heated in an oil bath at 50° C. for 24 hours (after approximately 0.75 hours, the polymer begins to precipitate). The polyhemiaminalP-1 was precipitated in acetone or water, filtered and collected to yield 0.22 g, >98% yield as a white solid.

A second exemplary PHA material may be prepared by reaction of 4,4'-methylenedianiline (MDA) with PF:

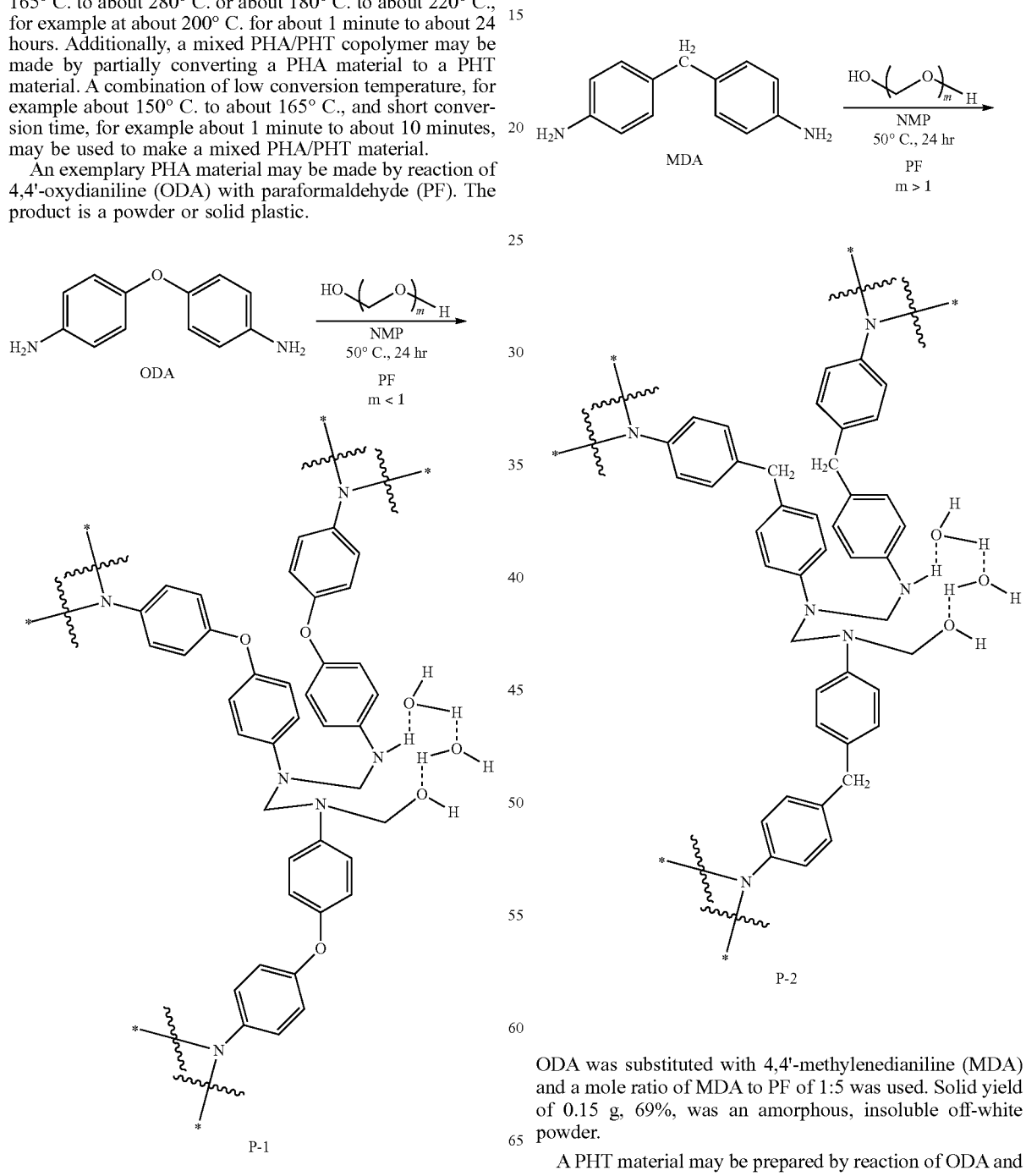

ODA was substituted with 4,4'-methylenedianiline (MDA) and a mole ratio of MDA to PF of 1:5 was used. Solid yield of 0.15 g, 69%, was an amorphous, insoluble off-white powder.

A PHT material may be prepared by reaction of ODA and PF, as follows:

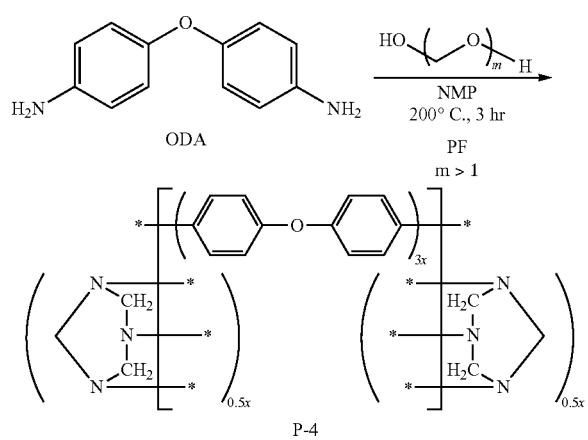

P-4

P-4, a polyhexahydrotriazine, was prepared by reaction of 4,4'-oxydianiline (ODA) with paraformaldehyde (PF). ODA (0.20 g, 1.0 mmol) and PF (0.15 g, 5.0 mmol, 2.5 eq.) were weighed out into a 2-Dram vial inside a $N_2$-filled glovebox. NMP (6.2 g, 6.0 mL, 0.17 M) was added. The reaction mixture was removed from the glovebox, and heated in an oil bath at 200° C. for 3 hours (after approximately 0.25 hours, the polymer begins to gel in the NMP). The solution was allowed to cool to room temperature and the polymer was precipitated in 40 mL of acetone, allowed to soak for 12 hours, then filtered and dried in a vacuum oven overnight and collected to yield 0.21 g, 95% yield of P-4 as an off-white solid.

The components of the supramolecular therapeutic agent delivery assembly described herein may be included in a composite material that may be used for therapeutic agent delivery. Any desired polymer may form a composite material with an HA, HT, or PHH material to provide selected properties. Carbon nanotubes may also form a composite with HA, HT, or PHH materials to provide additional mechanical integrity in therapeutic agent delivery applications.

At operation 140, a therapeutic agent may be incorporated into the supramolecular assembly. The therapeutic agent may be any biologically active material which can be utilized in therapeutic applications. Examples of the therapeutic agent include pharmaceuticals which are functionalized with nitrogen-containing groups, such as free amines. The therapeutic agent may be incorporated into the hydrophobic component of the supramolecular therapeutic agent delivery assembly covalently or otherwise physically mixed into the supramolecular therapeutic agent delivery assembly. The therapeutic agent may be covalently associated with the hydrophobic component in the supramolecular therapeutic delivery assembly. Various other interactions, such as hydrogen bonding, ionic interactions, dipole interactions, and Van der Waals interactions, between the therapeutic agent and the hydrophobic component may also function to incorporate the therapeutic agent in the supramolecular therapeutic delivery assembly.

At operation 150, the supramolecular therapeutic agent delivery assembly may be delivered to a biological target. The biological target may be a biological system, such as a human in vivo environment. In this embodiment, oral delivery of the supramolecular therapeutic agent delivery assembly in a pill or capsule is envisioned. However, the supramolecular therapeutic agent delivery assembly may also be configured for topical applications. In one embodiment, it may be desirable to deliver the therapeutic agent to the intestines where more desirable conditions for delivery of the therapeutic agent may be utilized. The PHT material of the supramolecular therapeutic agent delivery assembly is generally resistant to acidic conditions. For example, the PHT material will not decompose at pH=2, which is a similar pH to the acidic environment found in the stomach.

Similarly, the hydrophobic carbonate component may also be resistant to the acidic environment and the supramolecular therapeutic agent delivery assembly may pass through the stomach to the intestine where the pH is normally within the range of 7-8. The hydrophobic carbonate component may be susceptible to a more basic environment and may decompose in a different biological environment, such as the intestines. As a result of the decomposition of the hydrophobic carbonate component, which was primarily responsible for bonding or incorporating the therapeutic agent into the supramolecular therapeutic agent delivery assembly, the therapeutic agent may be released into the desired biological environment. The therapeutic agent may then diffuse across the endothelium of the intestines and enter the bloodstream. Upon release of the therapeutic, the unmetabolized hydrophilic and PHT material components of the supramolecular therapeutic agent delivery assembly may be expelled from the biological environment.

While the foregoing is directed to example embodiments of the present disclosure, other and further embodiments may be devised without departing from the basic scope thereof, and the scope thereof is determined by the claims that follow.

What is claimed is:

1. A method of preparing a micellar assembly, comprising:

providing a first mixture of a cyclic carbonate-containing material, a carbonate/PEG precursor, and a diamine material wherein the cyclic carbonate-containing material is formula (C):

(C)

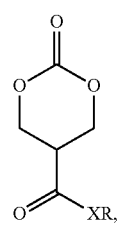

wherein X is —N(H)—, —O—, or —S—, and R is aryl or alkyl, and wherein the carbonate/PEG precursor is formula (B):

(B)

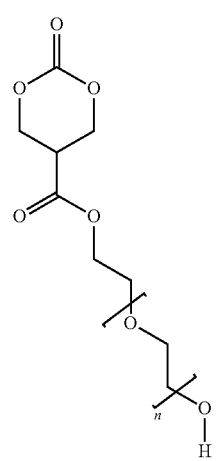

wherein n is an integer greater than 10, and wherein the diamine material is

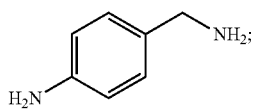

performing a ring opening polymerization from the first mixture to form a block co-polymer;

providing a trivalent bridging group monomer having the structure

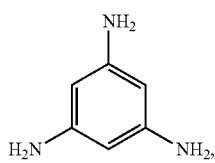

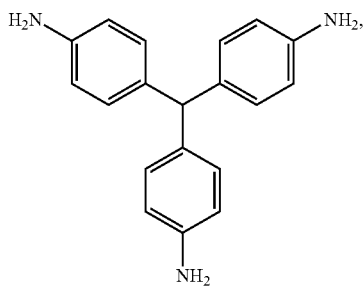

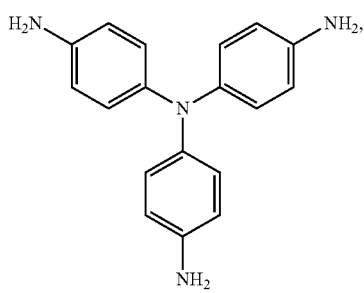

or combinations thereof;

providing a formaldehyde material; and performing a polyhexahydrotriazine polymerization process on a second mixture of the block co-polymer, the trivalent bridging group monomer, and the formaldehyde material to form a micellar assembly comprising a polyhexahydrotriazine material having a plurality of trivalent hexahydrotriazine groups having the structure

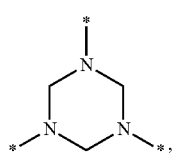

wherein each nitrogen of the trivalent bridging group is a nitrogen incorporated into one or more of the hexahydrotriazine groups after polymerization.

2. The method of claim 1, further comprising providing a divalent bridging group monomer in the polyhexahydrotriazine polymerization, the divalent bridging group monomer having the structure

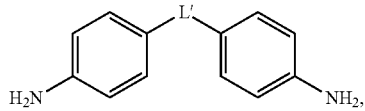

wherein L' is a divalent linking group selected from —O—, —S—, —N(R')—, —N(H)—, —R"—, and combinations thereof wherein R' and R" each independently comprise at least one carbon and are each independently selected from the group consisting of methyl, ethyl, propyl, isopropyl, phenyl, and combinations thereof.

3. The method of claim 2, further comprising providing a diluent group monomer in the polyhexahydrotriazine polymerization, the diluent group monomer comprising an aromatic primary amine.

4. The method of claim 1, further comprising providing a diluent group monomer in the polyhexahydrotriazine polymerization, the diluent group monomer comprising an aromatic primary amine.

5. The method of claim 1, wherein a therapeutic agent is covalently linked to a hydrophobic component of the micellar assembly, the therapeutic agent comprising a free amine.

6. The method of claim 1, wherein performing the polyhexahydrotriazine polymerization process further comprises adding to the second mixture a solvent selected from the group consisting of N-methyl-2-pyrrolidone (NMP), dimethylsulfoxide (DMSO), N,N-dimethylformamide (DMF), N,N-dimethylacetamide (DMA), propylene carbonate (PC), N-cyclohexyl-2-pyrrolidone (CHP), N,N'-dimethylpropyleneurea (DMPU), and propylene glycol methyl ether acetate (PGMEA).

7. The method of claim 6, wherein the second mixture is heated at a temperature of about 50° C. to about 200° C. for about 1 minute to about 24 hours.

8. A method of preparing a micellar assembly, comprising:

providing a first mixture of a cyclic carbonate-containing material, a carbonate/PEG precursor, and a diamine material wherein the cyclic carbonate-containing material is formula (C):

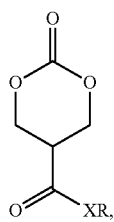

(C)

wherein X is —N(H)—, —O—, or —S—, and R is aryl or alkyl, and wherein the carbonate/PEG precursor is formula (B):

(B)

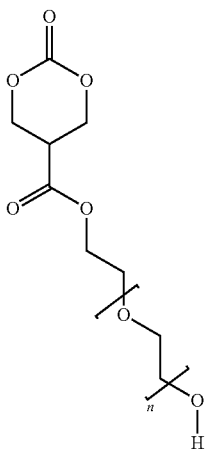

wherein n is an integer greater than 10, and wherein the diamine material is

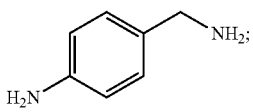

performing a ring opening polymerization from the first mixture to form a block co-polymer;
providing a trivalent bridging group monomer having the structure

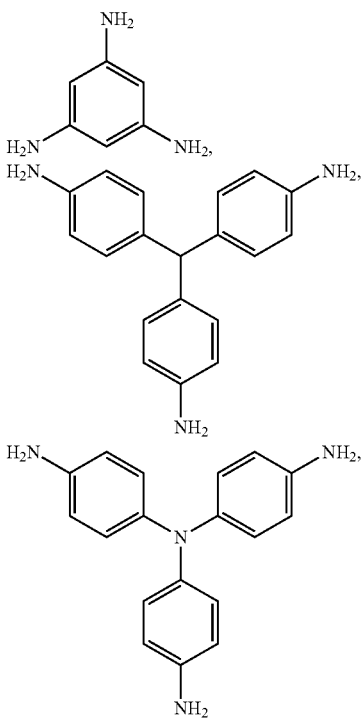

or combinations thereof;
providing a formaldehyde material;
performing a polyhexahydrotriazine polymerization process by reacting the block co-polymer, the trivalent bridging group monomer, the formaldehyde material in a second material to form a micellar assembly comprising a polyhexahydrotriazine material having a plurality of trivalent hexahydrotriazine groups having the structure

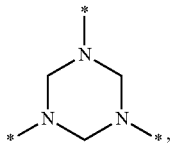

wherein each nitrogen of the trivalent bridging group is a nitrogen incorporated into one or more of the hexahydrotriazine groups after polymerization; and
incorporating a therapeutic agent into the micellar assembly.

9. The method of claim 8, further comprising providing a divalent bridging group monomer in the polyhexahydrotriazine polymerization, the divalent bridging group monomer having the structure

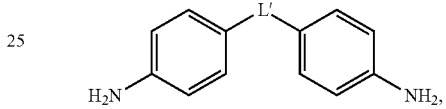

wherein L' is a divalent linking group selected from —O—, —S—, —N(R')—, —N(H)—, —R"—, and combinations thereof wherein R' and R" each independently comprise at least one carbon and are each independently selected from the group consisting of methyl, ethyl, propyl, isopropyl, phenyl, and combinations thereof.

10. The method of claim 9, further comprising providing a diluent group monomer in the polyhexahydrotriazine polymerization, the diluent group monomer comprising an aromatic primary amine.

11. The method of claim 8, wherein a therapeutic agent is covalently linked to a hydrophobic component of the micellar assembly, the therapeutic agent comprising a free amine.

12. The method of claim 1, further comprising physically mixing a therapeutic agent into the micellar assembly.

13. The method of claim 12, wherein the therapeutic agent comprises a free amine.

14. A method of preparing a micellar assembly, comprising:
providing a first mixture of a cyclic carbonate-containing material, a carbonate/PEG precursor, and a diamine material wherein the cyclic carbonate-containing material is formula (C):

(C)

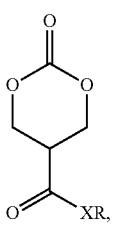

wherein X is —N(H)—, —O—, or —S—, and R is aryl or alkyl, and wherein the carbonate/PEG precursor is formula (B):

(B)

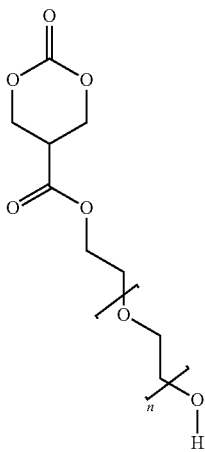

wherein n is an integer greater than 10, and wherein the diamine material is

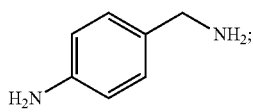

performing a ring opening polymerization from the first mixture to form a block co-polymer;
providing a trivalent bridging group monomer having the structure

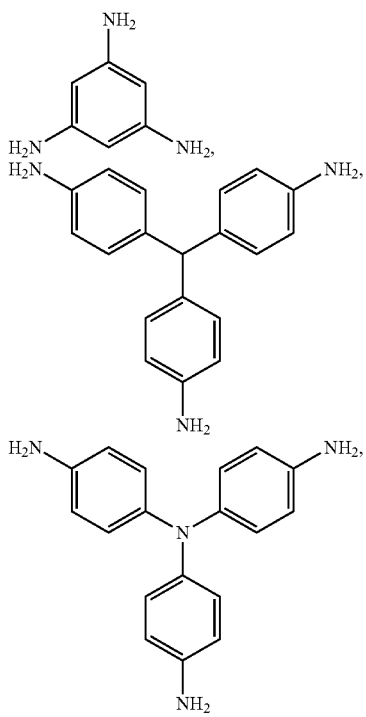

or combinations thereof;
providing a diluent monomer comprising an aromatic primary amine;

providing a formaldehyde material; and
performing a polyhexahydrotriazine polymerization process on a second mixture of the block co-polymer, the trivalent bridging group monomer, the diluent group monomer, and the formaldehyde material to form a micellar assembly comprising a polyhexahydrotriazine material having a plurality of trivalent hexahydrotriazine groups having the structure

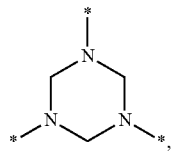

wherein each nitrogen of the trivalent bridging group is a nitrogen incorporated into one or more of the hexahydrotriazine groups after polymerization and a plurality of diluent group monomers; and
incorporating a therapeutic agent into the micellar assembly, the therapeutic agent comprising a free amine.

15. The method of claim 14, wherein the diluent group monomer is selected from the group consisting of

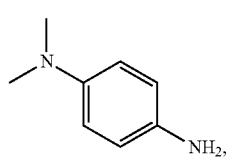 (MTA)

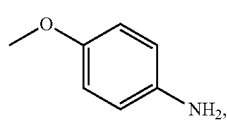 (DPD)

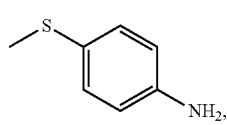 (MOA)

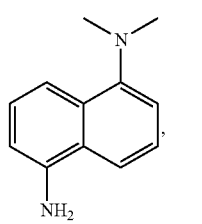 (15DMN)

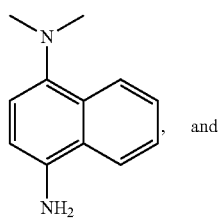 (14DMN)

, and

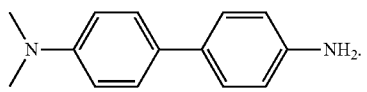 (DMB)

* * * * *